(12) United States Patent
Stoll

(10) Patent No.: US 7,135,042 B2
(45) Date of Patent: Nov. 14, 2006

(54) SURGICAL IMPLANT

(75) Inventor: Thierry Stoll, Sutz (CH)

(73) Assignee: HFSC Company, West Chester, PA (US)

( * ) Notice: Subject to any disclaimer, the term of this patent is extended or adjusted under 35 U.S.C. 154(b) by 0 days.

(21) Appl. No.: 10/508,024

(22) PCT Filed: Jan. 16, 2003

(86) PCT No.: PCT/CH03/00020

§ 371 (c)(1),
(2), (4) Date: Nov. 12, 2004

(87) PCT Pub. No.: WO03/082160

PCT Pub. Date: Oct. 9, 2003

(65) Prior Publication Data

US 2005/0065604 A1   Mar. 24, 2005

(30) Foreign Application Priority Data

Mar. 30, 2002  (DE)  .......................... 202 05 016 U

(51) Int. Cl.
A61F 2/44  (2006.01)
(52) U.S. Cl. .................................. 623/17.11
(58) Field of Classification Search ............ 623/17.11, 623/17.16, 23.56, 23.61, 23.63
See application file for complete search history.

(56) References Cited

U.S. PATENT DOCUMENTS

| 4,815,454 | A | 3/1989 | Dozier et al. | |
| 5,769,897 | A | 6/1998 | Harle | |
| 5,865,845 | A | 2/1999 | Thalgott | |
| 5,888,222 | A | 3/1999 | Coates et al. | |
| 6,039,762 | A | 3/2000 | McKay | |
| 6,398,811 | B1* | 6/2002 | McKay | 623/17.16 |
| 6,485,517 | B1 | 11/2002 | Michelson | |
| 2001/0047208 | A1 | 11/2001 | Michelson | |
| 2003/0023306 | A1 | 1/2003 | Liu et al. | |
| 2003/0023312 | A1* | 1/2003 | Thalgott | 623/17.16 |
| 2005/0192669 | A1 | 9/2005 | Zdeblick et al. | 623/17.11 |

FOREIGN PATENT DOCUMENTS

WO   98/56319   * 12/1998

* cited by examiner

Primary Examiner—Bruce Snow
(74) Attorney, Agent, or Firm—Jones Day

(57) ABSTRACT

A surgical implant (1) in the form of an intervertebral implant defines a cavity (2) designed to receive bone replacement materials. The bone replacement material is entirely synthetic. With the surgical implant of the present invention, the danger of infection attending a natural bone replacement material is eliminated and, by selecting a synthetic bone replacement material, its physical properties (porosity, pore size, mechanical strength) are no longer exposed to fluctuations.

22 Claims, 1 Drawing Sheet

SURGICAL IMPLANT

The present invention relates to a surgical implant defined in the preamble of claim 1, in particular to an intervertebral implant, an intramedullary pin or an intrajoint prosthesis.

Intervertebral implants or other surgical implants comprising cavities designed to be traversed by bones in most instance will be filled during surgery with bones or bony materials in order to allow optimal bone growth through them (the so-called fusion of two vertebras in the case of two vertebras).

The state of the art includes the following procedures:

(a) filling with autologuous bone chips removed from the patient's iliac crest; this procedure frequently correlates with additional patient morbidity, (b) filling the implants with autologuous bone removed from the adjacent vertebra as regards intervertebral implantations with anterior access, (c) implant filling using a bony material; this material may be natural or entirely synthetic; if natural, there is a residual danger of infection both for an allogenic and a xenogenic material; moreover the physical properties of a bone-replacement material may fluctuate substantially when involving the various donor individuals and body removal sites.

The above state of the art is merely cited as background of the present invention and should not be construed having been actually published or being widely known at the time this application was filed.

The objective of the present invention is palliation. It aims to create an implant which when being implanted already contains an entirely synthetic bone replacement material even in the form of a composite product.

The above problem is solved by the present invention by an implant defined by the features of claim 1.

By resorting to an entirely synthetic bone replacement material, the invention allows averting all above cited drawbacks. As a result it also offers the advantage that—compared to natural bone replacement products—the danger of disease communication is precludes because of the absence of pathogenic proteins, germs, viruses or bacteria.

Preferably the entirely synthetic bone replacement material is made of a calcium phosphate, typically a beta tricalcium phosphate. This feature offers the advantage of using a ceramic of which the stoichiometric composition substantially corresponds to that of the human bone. Furthermore the time of degradation of beta tricalciumphosphate is neither too short nor too long, and consequently cavities or implant residues are averted in the course of degradation.

Also the present invention offers further advantages to the patient. In particular, on account of simplified surgery, (a) the time of surgery is substantially shortened, (b) the time under anesthesia is less, and (c) the patient suffers less loss of blood, and, by selecting a synthetic bone replacement material, the properties of said material (porosity, pore size, mechanical compressive strength) are not subjected to fluctuations.

The bone replacement material may be in the form of a rigid element corresponding to the cavity geometry or alternatively in the form of a plastically deforming mass that can be introduced into said cavity.

In a particular embodiment mode, the implant cavity flares conically or cuneately toward the top or the bottom implant surface. As a result the entirely synthetic bone replacement material element inserted into said cavity is press-fitted into the cavity.

However the element also may be affixed by an appropriate fastener, preferably a screw or pin or a stop in the said cavity.

The implant of the invention may comprise a single cavity or several, typically in the latter case from two to eight mutually separate cavities.

Preferably the implant is designed as an intervertebral implant, though it also may be an intramedullary pin or in the form of another osteosynthetic implant or an intrajoint prosthesis.

In one embodiment of the present invention in the form of an intervertebral implant, same is preferably designed as a spacer unit comprising a top and a bottom surface which are appropriate to rest against the end plates of two adjacent vertebras. In this design the cavity does link the spacer unit's top surface to its bottom surface. Appropriately the top surface and/or the bottom surface of said spacer unit are structured in three dimensions, for instance being fluted, grooved, nubbed or in the form of other elevations or indentations.

Preferably the implant shall be transparent to x-rays, in particular consisting of a polymer such as PEEK. The advantage is that fusion may be assessed clinically.

In a further embodiment mode of the present invention, the bone replacement material is resorbing, preferably being hydroxyl apatite or tricalcium phosphate. This feature offers the advantage that because of material resorption, new bone tissue may grow back and need not force itself through the permanent material's pores.

The bone replacement material element advantageously exhibits a porosity of at least 25%, typically at least 35%, at least 50% of the pores exhibiting a diameter preferably in the range of 200 to 500µ.

In a further embodiment mode, the bone replacement material exhibits connections between the individual pores having diameters in the range of 10 to 500µ, preferably 200 to 400µ.

Illustratively the implant may be implemented in that a rigid element corresponding to the cavity geometry and made of an entirely synthetic bone replacement material is pressed into the implant cavity or affixed therein by appropriate fasteners. In another procedure, a moldable and preferably kneadable mass of an entirely synthetic bone replacement material preferably in granular form is introduced into the cavity where it shall be left in the uncured or cured state. This latter procedure also is appropriate for filling the cavities with bone replacement material during surgery.

The invention and its further embodiments are elucidated below in relation to the partly diagrammatic representation of an illustrative embodiment.

Figure 1:
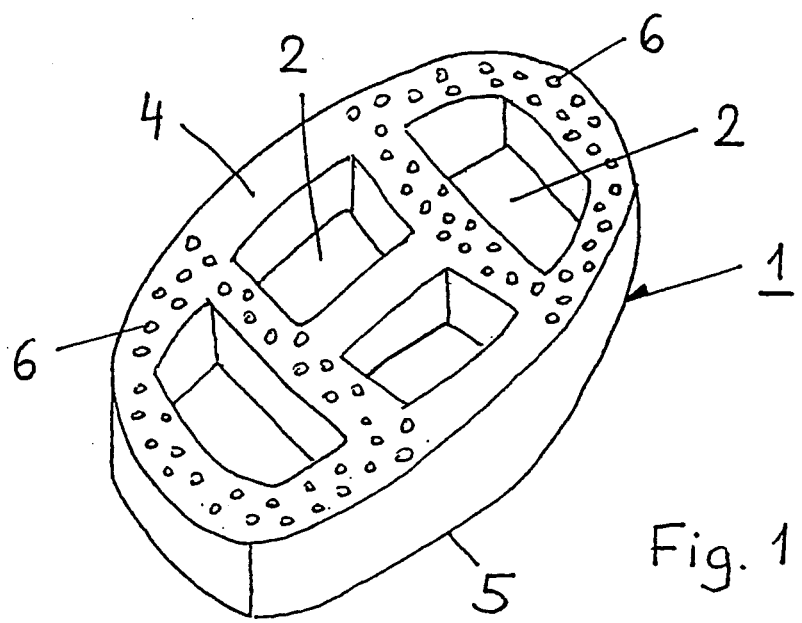
FIG. 1 is a perspective of the implant in its unfilled state.
Figure 2:
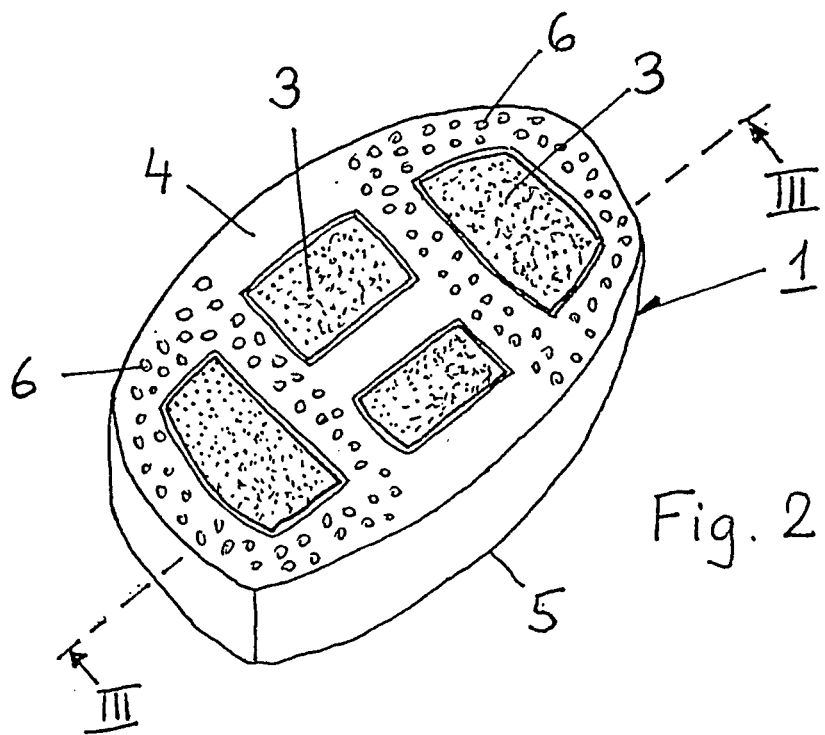
FIG. 2 is a perspective of the implant in its filled state.
Figure 3:
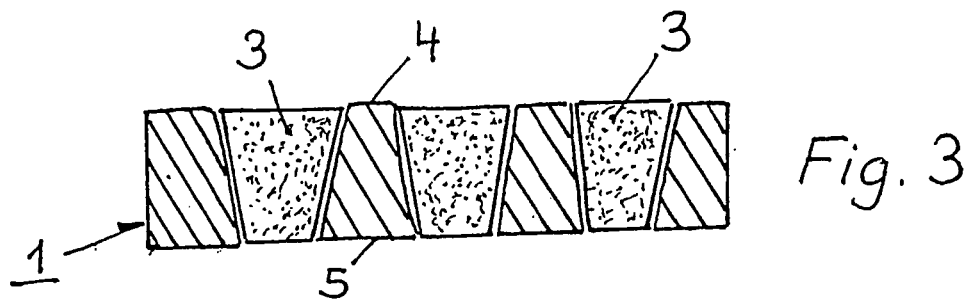
FIG. 3 is a longitudinal section along line III—III through the implant of FIG. 2.

The implant shown in FIGS. 1 through 3 is an intervertebral implant in the form of a spacer unit comprising four mutually separate cavities 2 that connect the top surface 4 to the bottom surface 5 of the spacer unit. The top surface 4 and the bottom surface 5 are designed to rest against the end plates of two adjacent vertebras and are fitted in part with a 3-dimensional structure 6 in the form of nubs.

As shown by FIG. 3, the cavities 2 flare conically or cuneately or in the form of pyramidical frustra toward the surface 4 of the implant 1 and they contain, as shown in FIG. 2, geometrically corresponding elements 3 made of an entirely synthetic bone replacement material. The elements 3 rest in press-fitted manner in the cavities 2.

The spacer unit is made of PEEK whereas the elements 3 are made of porous hydroxyl apatite.

The invention claimed is:

1. A surgical implant comprising:
   a top surface and a bottom surface; and
   at least one cavity which connects the top surface to the bottom surface,
   wherein walls of the at least one cavity are tapered in a form of a pyramidical frusta such that the top surface opening is larger than the bottom surface opening, and
   wherein the at least one cavity is filled with synthetic bone replacement material.

2. An implant according to claim 1, wherein the implant comprises between two and eight mutually separated cavities.

3. An implant according to claim 1, wherein the implant is formed from an x-ray transparent material.

4. An implant according to claim 3, wherein the implant is formed from a PEEK polymer.

5. An implant according to claim 1, wherein the implant is designed as an intervertebral implant.

6. An implant according to claim 5, wherein the implant is designed as a support unit wherein the top surface and the bottom surface are operable to rest against end plates of two adjacent vertebrae.

7. An implant according to claim 6, wherein at least one of the top surface and the bottom surface comprise three-dimensional structures.

8. An implant according to claim 7, wherein the three-dimensional structures are in the form of nubs.

9. An implant according to claim 1, wherein the bone replacement material is a rigid element corresponding to a geometry of the cavity.

10. An implant according to claim 9, wherein the element is press fit into the cavity.

11. An implant according to claim 9, wherein the element is secured in the cavity by a fastener.

12. An implant according to claim 9, wherein the element is made of a bone replacement material consisting at least partly of a bio-resorbable material selected from a group consisting at least of hydroxyl apatite and tricalcium phosphate.

13. An implant according to claim 12, wherein the bio-resorbable material is selected from the group consisting of hydroxyl apatite and tricalcium phosphate.

14. An implant according to claim 9, wherein the element is made of a bone replacement material having a porosity of between about 25% and about 35%.

15. An implant according to claim 9,
   wherein the element is made of a porous bone replacement material, and
   wherein at least 50% of the pores of the bone replacement material have a diameter in the range of about 200 to about 500μ.

16. An implant according to claim 9, wherein the element is made of a bone replacement material having individual pores connected to each other, the pores having a diameter in the range of about 10 to about 500μ.

17. A method to manufacture an implant as claimed in claim 9, comprising the steps of:
   forming the rigid element from entirely synthetic bone replacement material that corresponds to a geometry of the cavity; and
   press-fitting the rigid element into the implant cavity.

18. A method to manufacture an implant according to in claim 17, further comprising the steps of:
   plastically deforming a mass of entirely synthetic bone replacement material; and
   introducing said bone replacement material into the cavity.

19. A method to manufacture an implant according to claim 18, wherein the synthetic bone replacement material structure is granular.

20. An implant according to claim 1, wherein the bone replacement material is a plastically deforming mass that can be inserted into the cavity.

21. A surgical implant comprising:
   a top surface and a bottom surface both designed to rest against an end plate of an adjacent vertebrae;
   at least one cavity which connects the top surface to the bottom surface; and
   a mass of synthetic bone replacement material, the bone replacement material being positioned inside the at least one cavity,
   wherein walls of the at least one cavity are tapered such that the top surface opening is larger than the bottom surface opening, and
   wherein the bone replacement material has a porosity of between about 25% and about 35%.

22. A surgical implant comprising:
   a top surface and a bottom surface both designed to rest against an end plate of an adjacent vertebrae;
   at least one cavity which connects the top surface to the bottom surface; and
   a mass of synthetic bone replacement material, the bone replacement material being positioned inside the at least one cavity,
   wherein walls of the at least one cavity are tapered in a form of a pyramidical frusta such that the top surface opening is larger than the bottom surface opening, and
   wherein the bone replacement material has individual pores connected to each other, the pores having a diameter in the range of about 10 to about 500μ.

* * * * *